United States Patent
Albertazzi

(10) Patent No.: US 11,160,649 B2
(45) Date of Patent: Nov. 2, 2021

(54) FLEXIBLE INTEGRAL INTRACORNEAL RING

(71) Applicant: Roberto Gustavo Albertazzi, Buenos Aires (AR)

(72) Inventor: Roberto Gustavo Albertazzi, Buenos Aires (AR)

(*) Notice: Subject to any disclaimer, the term of this patent is extended or adjusted under 35 U.S.C. 154(b) by 23 days.

(21) Appl. No.: 16/550,603

(22) Filed: Aug. 26, 2019

(65) Prior Publication Data

US 2021/0059809 A1   Mar. 4, 2021

(51) Int. Cl.
*A61F 2/14* (2006.01)
*A61L 31/06* (2006.01)

(52) U.S. Cl.
CPC .............. *A61F 2/147* (2013.01); *A61L 31/06* (2013.01); *A61F 2220/0033* (2013.01); *A61F 2250/006* (2013.01)

(58) Field of Classification Search
CPC ............................................ A61F 2/145–2/147
See application file for complete search history.

(56) References Cited

U.S. PATENT DOCUMENTS

| 6,171,336 B1 * | 1/2001 | Sawusch | A61F 2/147 128/898 |
| 6,508,837 B1 * | 1/2003 | Silvestrini | A61F 9/0017 623/5.11 |

FOREIGN PATENT DOCUMENTS

WO   WO-2017117689 A1 *   7/2017   ............. A61F 2/147

* cited by examiner

*Primary Examiner* — Leslie Lopez
(74) *Attorney, Agent, or Firm* — Defillo & Associates, Inc; Evelyn A Defillo

(57) ABSTRACT

A flexible integral intracorneal ring for the treatment and correction of vision disorders and corneal malformations, which is annular, continuous or integral and flexible, all of which allows to inject the ring into the stroma thanks to its outstanding flexibility due to its structural design and also allows to increase your rigidity when inserted.

6 Claims, 6 Drawing Sheets

US 11,160,649 B2

FLEXIBLE INTEGRAL INTRACORNEAL RING

FIELD OF THE INVENTION

The present invention relates to an intracorneal or intrastromal implant ring for the treatment and correction of vision disorders and corneal malformations and, more particularly the invention relates to an intrastromal insert which is annular, continuous or integral and flexible, all of which allows to inject the ring into the stroma thanks to its outstanding flexibility due to its structural design and also allows to increase its rigidity when inserted.

DESCRIPTION OF THE PRIOR ART

Intracorneal or intrastromal rings are well known in ophthalmic implant techniques. These rings are in fact inserts or segments in the form of circular arc or annular methacrylate sectors used in ophthalmology as a surgical alternative to avoid keratoplasty in the treatment of corneal ectasias. Once implanted, they have the function of regularizing the surface of the cornea to try to stop the evolution of the pathology. They partially or totally correct the astigmatism characteristic of keratoconus disease, thus improving visual acuity.

The surgeon places them facing each other in a way to form a ring inside the cornea, in its peripheral area, guided by a pre-dissected channel with a specific dissector that makes a tunnel in the cornea. Among the most frequent interventions are patients affected by keratoconus, marginal degeneration, pelucidae, and corneal irregularities that occur after having undergone laser surgery, or corneal grafting.

The intracorneal segments were used for forty years for different purposes, such as dissected corneal stroma and made of different materials, such as polysulfones and different types of acrylics.

Different diameters have been used, such as 5, 6, 7, and 8 mm, different profiles, such as flat profiles with 0° inclination and conical with 17° and 34° inclination, and different geometric designs, such as triangular, trapezoidal; fusiform; hexagonal, bases of 600 microns, 800 microns, 900 microns and even 1330 microns, to achieve different effects in the cornea where they are inserted. These shape characteristics will be chosen according to the degree and type of corneal deformation of the patient.

Over time, precise technical details were known that have reduced complications and have gained a space for the treatment of low myopias and corneal ectasias. The acrylic material within the deep corneal stroma proved to be well tolerated, improving corneal curvature and visual acuity.

All these implants are rigid, static, and were always implanted in the tissue with manual surgical techniques, which needed a precise perpendicular cut to the stroma to make a 360° tunnel from there, in two semicircles, either manually or automated, assisted by perilimbar suction rings. The advent of the Femtosecond Lasers to ophthalmologic surgery did not change the technique, but it was now repeated more accurately using the precision that Laser technology has provided, but the way in which doctors operate is not modified.

As an example of intrastromal rings, a ring formed by articulated connected segments can be mentioned, described in WO 2017/117689 of the same inventor as the present one.

WO 95/03747 discloses a segmented and foldable intrastromal insert consisting of a succession of interconnected pieces to be implanted within the stroma.

Finally, EP 3492052 A1, also from the same inventor as the present one, discloses an implantation device of intrastromal segments and a family of rigid segments with grooves in the peripheral or external side thereof to provide injecting them and wherein their ends are flat to favor their horizontal stacking in the same channel, being segments of different arcs.

Even though these ring-forming inserts have worked with very good results in implant techniques so far, today it is necessary to have a new continuous or integral annular insert, that is to say, not formed by segments, which allows a better and more complete use of the laser techniques available today.

SUMMARY OF THE INVENTION

It is therefore an object of the present invention to provide an intracorneal annular insert or intrastromal ring to be implanted within a pre-dissected channel in the thickness of the cornea to modify its geometry for corrective purposes, where the insert comprises a single piece that has two free ends that are connected to form a complete ring once installed in the cornea.

It is also an object of the present invention to provide an intrastromal or intracorneal ring to be implanted within a pre-dissected channel in the thickness of the cornea and comprising a single piece that has radial cuts that provide flexibility before implantation and inner inserts that provide the rigidity once implanted in the cornea.

It is also an object of the present invention to provide a flexible integral intracorneal ring to be implanted in the cornea to modify its geometry for corrective purposes, wherein the ring comprises an elongated piece that has two connectable free ends to form a ring once installed in the cornea, said elongated part having an outer initial periphery with radial cuts and a continuous inner initial periphery, wherein the elongated piece has two positioning through holes or orifices for proper alignment.

BRIEF DESCRIPTION OF THE DRAWINGS

For greater clarity and understanding of the object of the present invention, it has been illustrated in several figures, in which it has been represented in one of the preferred embodiments, all by way of example, where.

DETAILED DESCRIPTION OF THE INVENTION

Referring to the figures, the invention consists of a new intrastromal ring to be implanted in the cornea to modify its geometry for corrective purposes, which thanks to its continuous or integral geometry constituted by a single piece, which could be assisted in its design by the clinical, corneal topographic and corneal tomographic studies of the patient to be treated, thus facilitating the treatment and correction of vision disorders and corneal malformations in a much more practical, efficient and predictable manner.

Figure 1:
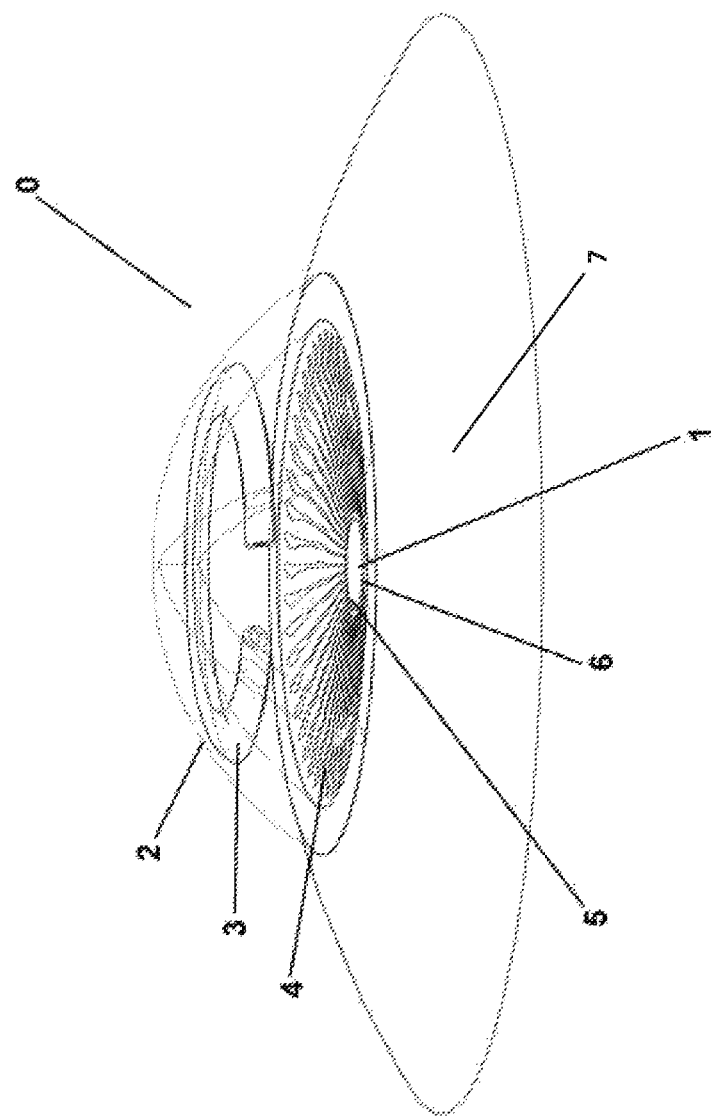
FIG. 1 is a partial section of a human eye showing the cornea that has also been cut in a circular portion thereof to illustrate an intracorneal ring implanted within the cornea.
Figure 2:
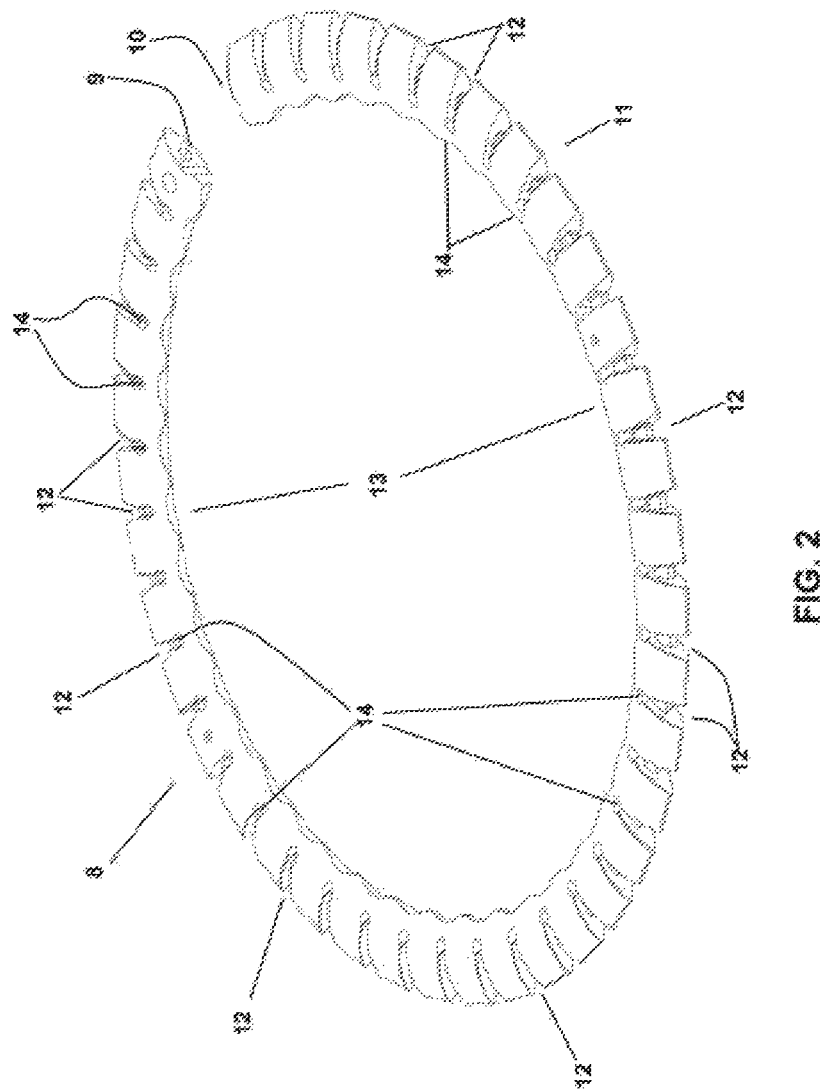
FIG. 2 is a perspective view of the intracorneal ring of the present invention showing it schematically in its manufacturing form and before its implantation in the cornea, where it is seen that the outer initial periphery presents radial cuts while the inner initial periphery is continuous.
Figure 3:
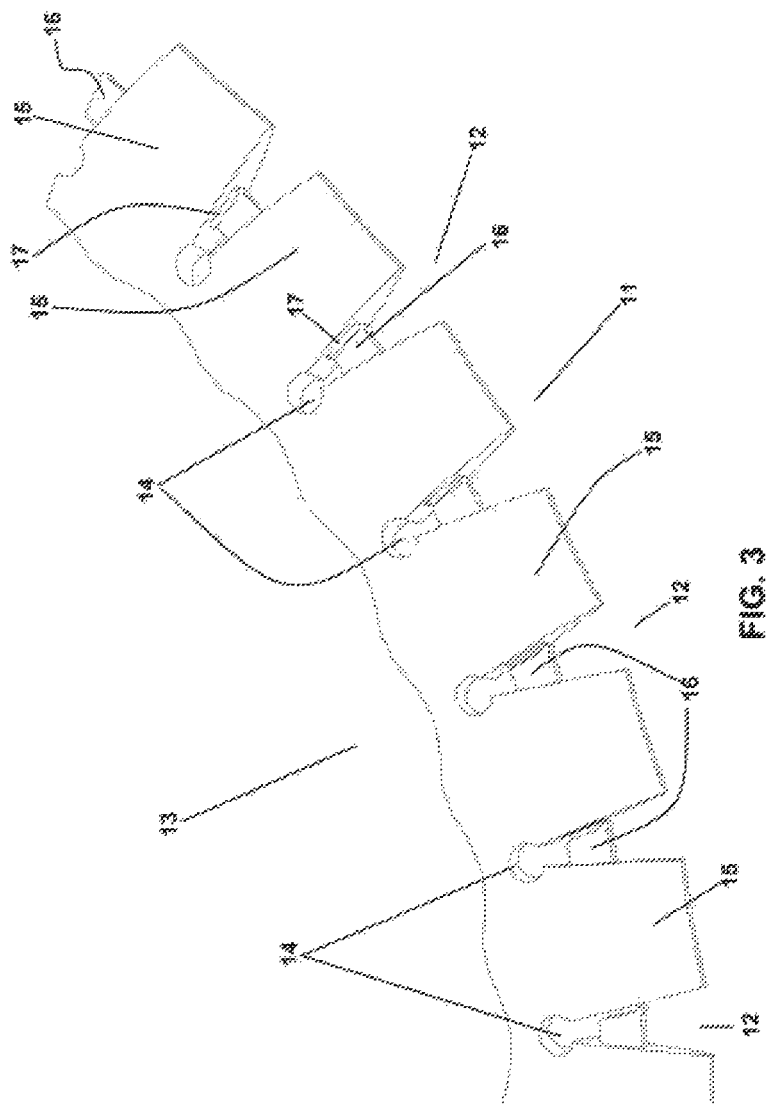
FIG. 3 is a plan view taken from above of a portion of the ring of FIG. 2.
Figure 4:
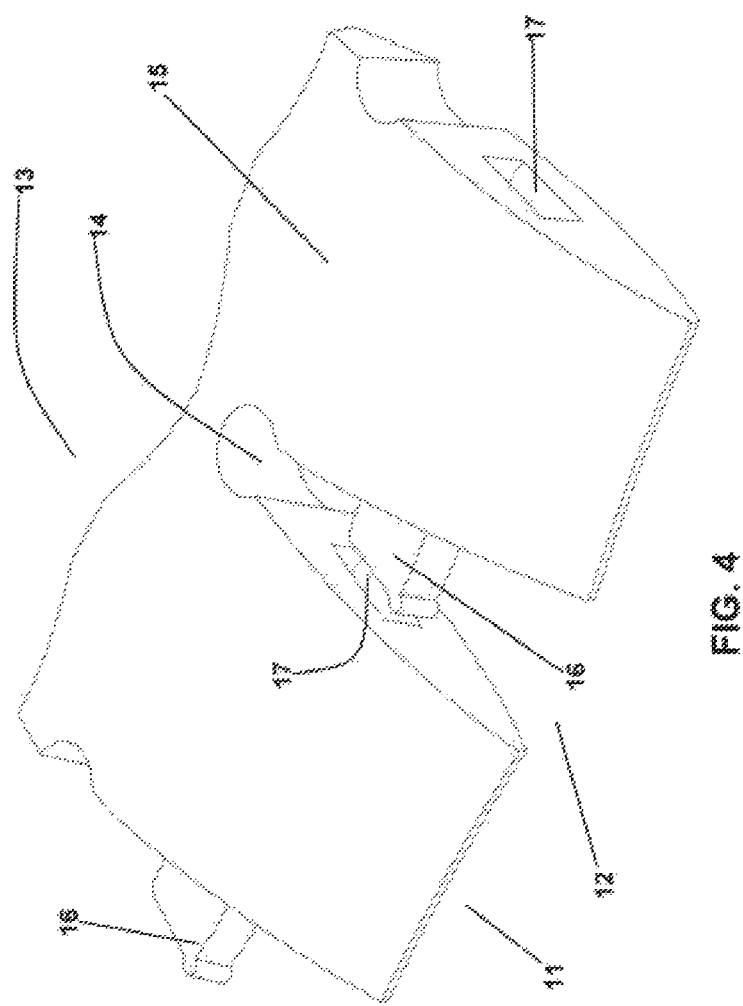
FIG. 4 is a detailed view of a portion of the ring of FIG. 2.

According to FIG. 1, a well-known "O" eye can be seen in the field of art, which in general features comprises a visual axis 1, cornea 2, intracorneal segment 3, iris 4, pupil 5, iris 6 and sclera 7. In said eye 1, and more particularly in the intracorneal segment 3 or in an annular portion of the intracorneal tissue surrounding the visual axis, the intrastromal ring of the present invention will be placed as indicated by general reference 8.

Wherein, said ring 8 comprises an elongated part having two free ends 9 and 10 connectable to form a ring once installed in the cornea, said elongated part having an outer initial periphery 11 with radial cuts 12 and a continuous inner initial periphery 13 which presents a wavy development by knurling that allows varying the height of the ring according to the corneal tomographic data obtained from the same place where it will be housed, plus a percentage to compensate for the compression of the tissue that hosts it, thus allowing its design to be assisted by tomography corneal.

Said radial cuts 12 have a stress relief end channel 14 in the form of a circular perforation that improves the ring flexibility and allows to change its angulation, thus modifying it and being possible to have different angles of corneal shock and these different angles will make it to have different effects on corneal curvature.

Between consecutive radial cuts 12 of the outer initial periphery 11, respective modules, teeth or links 15 are defined which each has lateral faces provided with corresponding male 16 and female 17 connectors, wherein the latter female connector 17 of one link 15 faces the male connector 16 of the subsequent link, but said arrangement does not limit the invention since other connection arrangements can be considered and used without any inconvenience.

Thus, when all male 16 and female 17 connectors are connected to each other, they jointly define an outer final periphery 19 and an inner final periphery 20. Where, said outer final periphery 19 is comprised of the continuous inner initial periphery, while said internal final periphery is comprised of the outer initial periphery, as best illustrated in FIG. 5.

Figure 5:
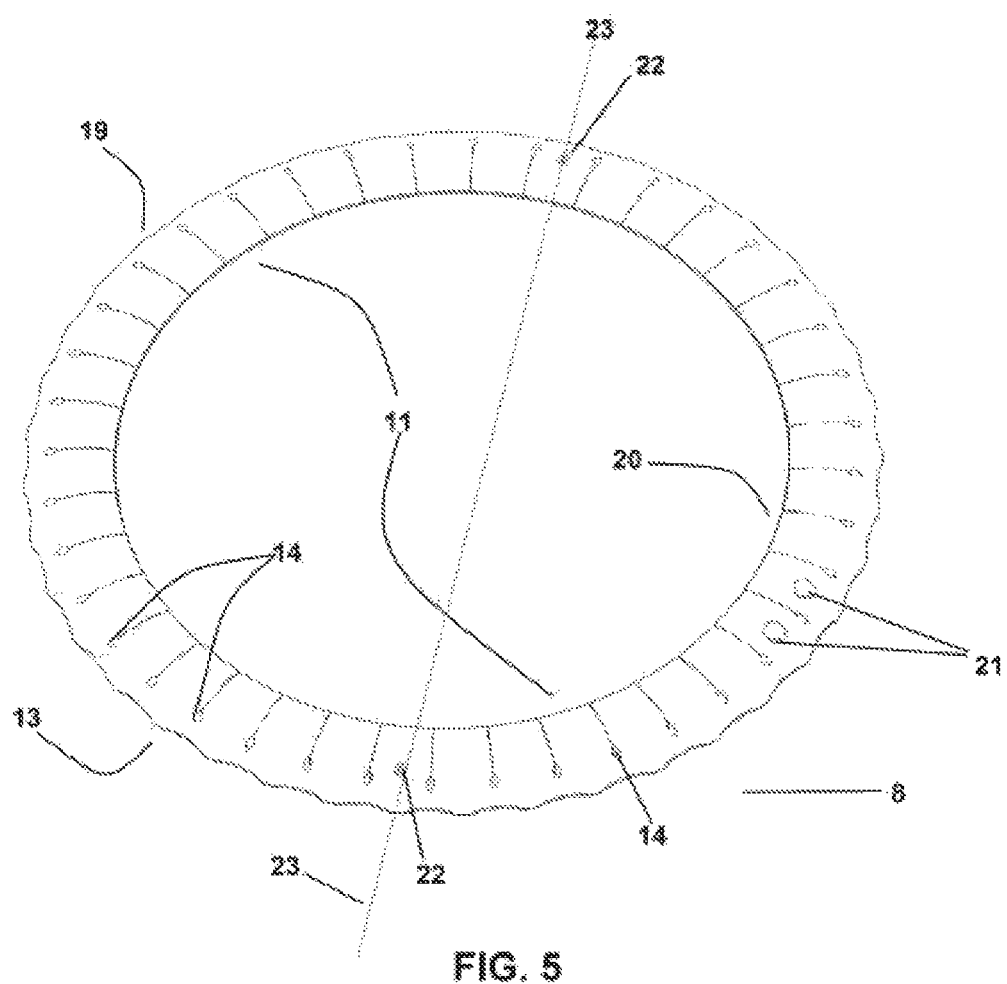
FIG. 5 is a perspective view of the intracorneal ring of FIG. 2 showing it in the closed configuration it presents once implanted, here it is clearly seen that the outer initial periphery, which presents the radial cuts, is now the inner final periphery, and the initial inner periphery, which is continuous, is now the final outer periphery, showing, in its thickness, two positioning through holes or orifices for proper alignment.
Figure 6:
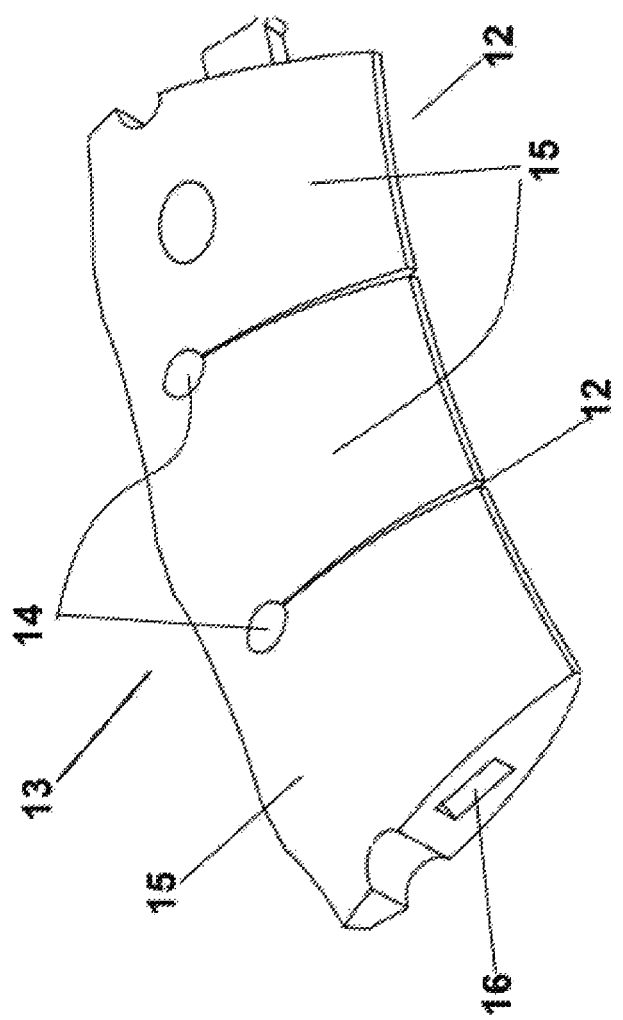
FIG. 6 is a detailed view of a portion of the ring of FIG. 5 in its closed configuration.

In addition, the flexible implant of the invention has two through holes 21, one in each module, tooth or link, as seen in FIG. 5, and which help to close the circle or ring once it has been placed in position. On the other hand, two equidistant holes 22 are provided which, once the ring is closed, are aligned along an imaginary axis or line 23 that crosses entirely the circumference, which must coincide in alignment with the implant in its correct position, since the modules, teeth or links created have or may have asymmetries in their production to correct or remedy the corneal asymmetries that the disease produces.

The use of male and female connectors allows the generation of "auto-inserts" to increase the rigidity of the ring once placed, allowing its radial and vertical cuts to be varied to thus modify its angulation when folded.

It is noted that the ring of the present invention can be made of a material with similar biological and structural behavior such as the linear isotactic polypropylene crystalline stereoisomer (Prolene) or of similar characteristics with respect to the corneal tissue reaction, not being limited to the same since other compatible materials can also be used without any inconvenience. Preferably for the present invention, but not limited to, a flexible, biocompatible or similar material to the behavior of polystyrene (PROLENE), preferably of fusiform profile, has been used to achieve that the invention is an injectable corneal insert, of varying thickness, with possible variation of the angle of corneal shock, from a plane like 0° to 35°, and that also thanks to the radial cuts increases the rigidity once placed in its definitive place.

That is, the arrangement of the radial cuts allows obtaining an insert composed of one piece, injectable and capable of having different angles of corneal shock—these different angles will have different effects on the corneal curvature to which it underlies (they will have 360°) and will be rigid once placed in its final place.

Thus, when the ring is manufactured, it presents the arrangement illustrated in FIGS. 2, 3, 4 and 6, in which it has the outer initial periphery provided with radial cuts and the continuous inner initial periphery.

However, the ring of the invention will have another arrangement within the pre-dissected channel in the thickness of the cornea. To do this, the professional in charge must first make said pre-dissected channel using FEMTO LASER and then implant the ring of the invention. Then, the implantation of the ring will be carried out through an incision of the sclerocorneal limbus with the assistance of the FEMTO Laser technology commonly used in ophthalmology, and the help of an injector for capsular expansion rings, or the like, leaving the ring of this form with the arrangement illustrated in FIG. 5.

According to the prior art, it is known that intracorneal segments can generally have different profiles of inclination, design and base. The intracorneal segments are small implants of rigid medical grade acrylic (PMMA) which pass the tolerance and compatibility tests with the corneal tissue where they are housed.

Since they are rigid, when implanted in a viscoelastic structure in the shape of a prolata ellipse such as the cornea, it deforms this structure, in different ways, depending on the implants. For example, flat implants have an effect, while conical ones with inclinations ranging from 17° and 34° will have other effects.

The segments act by different mechanisms, one is due to the thickness changes of the same, being greater thickness greater effect, less thickness less effect. Its effect also changes according to the diameter, the smaller the diameter, the greater the effect, and the greater the diameter, the smaller the effect.

Another mechanism by which they act is through the so-called arc shortening by which all increase the tension of the collagen fibers of the anterior stroma producing flattening. The more flat the angulation of the segment with respect to the horizontal axis, the greater the effect of a corneal planning, as it performs strength against the physiological angulation of the cornea.

Moreover, the links or segments, by design, are rigid to the upper-lower torsion, a necessary characteristic to have a lasting corneal effect. However, they are not rigid laterally, necessary characteristic to be inserted. As it is formed by different modules, teeth or links, each of them presents different inclinations, designs and even different bases, in this way the volume and diameter also change. These changes could be assisted in its design by clinical, topographic and corneal tomography of the patient to be treated, thus creating a personalized method of treatment.

Due to FEMTO LASER technology; these segments, due to their injectable design, are implanted, from an incision far from where they do their effect, such as the corneal limbosclero, a much easier place to heal because it is next to the conjunctival stem cells and near the blood vessels, which makes the place more physiological advantageous, being that area where all cataract surgeries are performed.

The application of the implant object of the present invention is in the treatment of keratoconus. The keratoconus is a congenital, inherited disease that is characterized by a progressive non-inflammatory corneal deformation: it has 4 evolutionary stages going from a slight imperceptible corneal deformation to the loss of the corneal structure and function arriving to the necessity of a corneal graft, and that anyway has no cure now.

These types of deformations are totally asymmetric, central, paracentral and peripheral of which there are many descriptions and patterns described. The rigid segments that today are used, are to stabilize these deformations and even decrease them to be able to recover the lost vision by the deformations that the disease produces, these injectable segments have an incredible potential, because they can be customized for each deformation and each cornea, and even plan them using maps of curvatures and corneal thicknesses. The possibilities it offers are almost endless, because its design can be assisted with corneal tomography and topography.

The design of the segments included in the present implant allows an easy placement in a predetermined place, where the Femto Laser makes the tunnel and creates the channel where it is going to be placed, and once in that place the only strength necessary for its effect is that it opposes to the torsion that the tissue will undergo. It should be noted that the conventional segments of the prior art are made of rigid materials such as the current ones, that is, polymethylmethacrylate.

However, the present invention, being a ring of a single injectable piece with radial cuts and stress relief end channels, presents greater flexibility and better practicality at the time of implantation, achieving a final result that allows stabilizing in a better way and properly the deformations and even reduce them to recover the lost vision by the deformations that the keratoconus disease produces.

In addition, as mentioned above, the flatter the segment angulation is with respect to the horizontal axis, the greater the corneal flattening effect is obtained, and this is satisfactorily and efficiently achieved by the invention since it allows angles from 0° to 35°.

In this way, the intrastromal ring of the present invention is constituted and constructed, which, being annular, continuous or integral and flexible, can be injected into the stroma thanks to its outstanding flexibility due to its structural design, also increasing its rigidity when inserted to treat and correct vision disorders and corneal malformations.

The invention claimed is:

1. A flexible integral intracorneal ring designed to be implanted in a cornea to modify its geometry for corrective purposes, the flexible integral intracorneal ring comprising:
   an elongated piece having two free ends that are connected to form a ring once installed in the cornea;
   wherein said elongated piece has an outer initial periphery with consecutive radial cuts and a continuous inner initial periphery;
   wherein said elongated piece includes two positioning through-holes for correct alignment;
   wherein said radial cuts have a stress relief end channel in form of a circular perforation.

2. The intracorneal ring according to claim 1, wherein said elongated piece is made of a linear isotactic crystalline stereoisomer of polypropylene.

3. The intracorneal ring according to claim 1, wherein said continuous inner initial periphery has an undulating development.

4. A flexible integral intracorneal ring designed to be implanted in a cornea to modify its geometry for corrective purposes, the flexible integral intracorneal ring comprising:
   an elongated piece having tow free ends that are connected to form a ring once installed in the cornea;
   wherein said elongated piece has an outer initial periphery with consecutive radial cuts and a continuous inner initial periphery;
   wherein said elongated piece includes two positioning through-hole for correct alignment;
   wherein between the consecutive radial cuts of the outer initial periphery of the elongated piece, links are defined, each link having side faces provided with corresponding male and female connectors, wherein the female connector of each link faces the male connector of the subsequent link, that once locked in place, are crimped, coupled, or joined; and
   wherein, when all male and female connectors are connected to each other, and the elongated piece is rotated radially inwardly from an initial state, the outer periphery and the inner periphery flip and then the outer periphery becomes a final inner periphery and the inner periphery becomes a final outer periphery.

5. The intracorneal ring according to claim 4, wherein said outer final periphery is comprised of the continuous inner initial periphery, while said inner final periphery is comprised of the outer initial periphery.

6. A flexible integral intracorneal ring designed to be implanted in a cornea to modify its geometry for corrective purposes, the flexible integral intracorneal ring comprising:
   an elongated piece having two free ends that are connected to form a ring once installed in the cornea;
   wherein said elongated piece has an outer initial periphery with consecutive radial cuts and a continuous inner initial periphery;
   wherein said elongated piece includes two positioning through-hole for correct alignment;
   wherein said radial cuts have a stress relief end channel in the for of a circular perforation;
   wherein said radial cuts having the stress relief end channel in the form of the circular perforation, said radial cuts vary their angulation, from 0° to 40°, thus modifying a V opening and the radial cuts are configured to have different angles of corneal shock and these different angles will have different effects on corneal curvature.

* * * * *